United States Patent [19]

Lutz et al.

[11] Patent Number: 4,832,732
[45] Date of Patent: May 23, 1989

[54] 1-METHYL-1H-IMIDAZOLE-5-CARBOXYLIC ACID DERIVATIVES AND THEIR USE AS HERBICIDES

[75] Inventors: William R. Lutz, Riehen, Switzerland; Guy R. E. Van Lommen, Berlaar, Belgium; Victor Sipido, Merksem, Belgium; Wim G. Verschueren, Antwerpen, Belgium

[73] Assignee: Janssen Pharmaceutica N.V., Beerse, Belgium

[21] Appl. No.: 134,323

[22] Filed: Dec. 17, 1987

[30] Foreign Application Priority Data

Dec. 30, 1986 [GB] United Kingdom ............... 8631020

[51] Int. Cl.$^4$ ................ A01N 43/50; A01N 43/54; A01N 43/48; C07D 233/04; C07D 233/20; C07D 233/44; C07D 233/64; C07D 233/66

[52] U.S. Cl. ............................. 71/92; 71/88; 71/90; 71/94; 544/54; 544/55; 544/96; 548/125; 548/131; 548/146; 548/152; 548/179; 548/180; 548/202; 548/203; 548/204; 548/205; 548/217; 548/235; 548/236; 548/238; 548/252; 548/253; 548/254; 548/269; 548/317; 548/318; 548/320; 548/321; 548/324; 548/336; 548/337; 548/341; 548/255

[58] Field of Search ............ 548/336, 337, 131, 125, 548/146, 152, 179, 180, 202, 203, 204, 205, 217, 235, 236, 238, 252, 253, 254, 269, 317, 318, 320, 321, 324, 341; 71/90, 92, 94, 88; 544/54, 55, 96

[56] References Cited

U.S. PATENT DOCUMENTS 2,541,924  2/1951  Jones ................................. 548/321
3,354,173 11/1967  Godefroi et al. ................. 548/336
4,182,624  1/1980  Soder et al. ........................ 71/92

FOREIGN PATENT DOCUMENTS 191514  8/1986  European Pat. Off. ............ 548/336

Primary Examiner—Mary C. Lee
Assistant Examiner—J. Richter

[57] ABSTRACT

Novel herbicidal 1-methyl-1H-imidazole-5-carboxylic acid derivatives, compositions containing these compounds as active ingredients, and a method for controlling weeds, preferably selectively in crops of useful plants. Further the invention also relates to a process for making these novel compounds.

17 Claims, No Drawings

1-METHYL-1H-IMIDAZOLE-5-CARBOXYLIC ACID DERIVATIVES AND THEIR USE AS HERBICIDES

BACKGROUND OF THE INVENTION

In U.S. Pat. No. 3,354,173 there are described a number of 1H-imidazole-5-carboxylic acids possessing hypnotic properties. U.S. Pat. No. 4,182,624 discloses various imidazole-5-carboxylic acid derivatives having fungicidal, herbicidal and plant-growth regulant activity. Further, in Public. Eur. Pat. Appln. No. 0,191,514 a group of imidazole-5-carboximidates are taught to possess fungicidal activity.

DESCRIPTION OF THE INVENTION

The present invention is concerned with herbicidally active 1-methyl-1H-imidazole-5-carboxylic acid derivatives having the formula

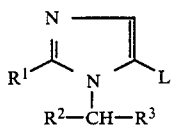
(I)

the stereoisomeric forms thereof, or the salts thereof, wherein $R^1$ is hydrogen or mercapto;

$R^2$ is hydrogen, $C_1-C_7$alkyl, $C_3-C_7$alkenyl, $C_3-C_7$alkynyl, $C_3-C_7$cycloalkyl, $C_5-C_7$cycloalkenyl; said $C_1-C_7$alkyl, $C_3-C_7$alkenyl, $C_3-C_7$alkynyl, $C_3-C_7$cycloalkyl, $C_5-C_7$cycloalkenyl being optionally substituted with one to three radicals independently selected from $C_1-C_5$alkyl, $C_1-C_5$alkyloxy, hydroxy$C_1-C_5$alkyl, $C_1-C_5$alkoxy$C_1-C_5$alkyl and halo;

$R^3$ is $C_4-C_{13}$alkyl, $C_3-C_7$cycloalkyl, or $C_5-C_7$cycloalkenyl each unsubstituted or substituted with one to three radicals independently selected from $C_1-C_5$alkyl, $C_1-C_5$alkyloxy, hydroxy$C_1-C_5$alkyl, $C_1-C_5$alkyloxy$C_1-C_5$alkyl and halo;

L is cyano, —COOR$^4$,

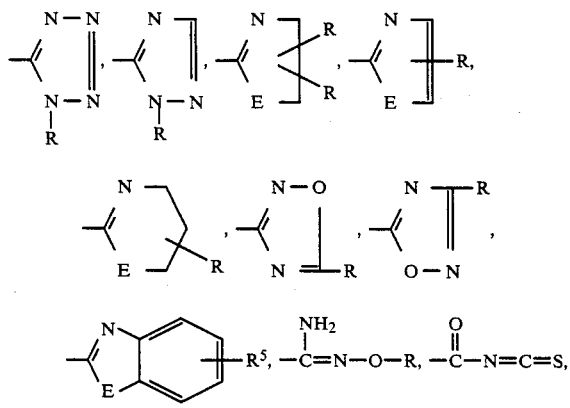

or a group —C(=G)—D—R$^6$;

$R^4$ is hydrogen, $C_1-C_7$alkyl, mono-, di- or trihalo-$C_1-C_5$alkyl, $C_3-C_7$alkenyl, $C_3-7$alkynyl, $C_3-C_7$cycloalkyl, $C_1-C_7$alkyloxy$C_1-C_7$alkyl or aryl$C_1-C_5$alkyl;

E is oxygen, sulfur or —NR—;

G is =N—R, oxygen or sulfur;

R is hydrogen or $C_1-C_5$alkyl;

D is sulfur, —N(R$^7$)—, —N(R$^8$)—NH—, —N(R$^8$)—O—,

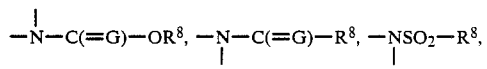

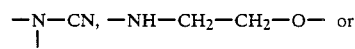

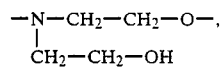

$R^6$, $R^7$ and each $R^8$ are independently selected from hydrogen, $C_1-C_5$alkyl, $C_3-C_5$alkenyl, $C_3-C_5$alkynyl, $C_3-C_7$cycloalkyl, or $C_1-C_5$alkyl substituted with aryl, $C_3-C_7$cycloalkyl, $C_3-C_7$cycloalkyloxy, $C_1-C_5$alkyloxy, hydroxy, carboxyl or $C_1-C_8$alkyloxycarbonyl; whereas $R^8$ may also be aryl; or $R^6$ and $R^7$ together with the nitrogen atom to which they are attached may form a piperidinyl, pyrrolidinyl, 2-oxopiperidinyl, 2-oxopyrrolidinyl, morpholinyl, thiomorpholinyl, piperazinyl or 4-($C_1-C_5$alkyl)piperazinyl ring, each unsubstituted or substituted with one to three $C_1-C_5$alkyl groups;

$R^5$ is hydrogen, $C_1-C_5$alkyl, $C_1-C_5$alkyloxy, halo, trifluoromethyl, difluoromethoxy, cyano, nitro, amino, mono- and di$C_1-C_5$alkylamino or $C_1-C_5$alkylcarbonylamino; and aryl is phenyl optionally substituted with one to three substituents each independently selected from $C_1-C_5$alkyl, $C_1-C_5$alkyloxy and halo.

Surprisingly, the compounds of formula (I) exhibit strong herbicidal properties, and are therefore useful to control weeds. This property gains importance by the fact, that some crops of useful plants are not damaged, or are only slightly harmed when treated with compounds of formula (I) at high dosages. Consequently, the compounds of formula (I) are valuable selective herbicides in crops of useful plants, such as sugar beet, rape, soybeans, cotton, sunflower, cereals, especially wheat, barley, rye and oats, rice, both upland rice and paddy rice, and maize. Especially in rice crops a broad range of application rates can be employed, preferably if the rice crops are transplanted rice crops, and if the compounds of formula (I) are applied after transplantation. In maize crops selective herbicidal action is observed both at preemergence and at postemergence treatment.

The active ingredients (a.i.) of formula (I) are usually applied at application rates of 0.01 to 5.0 kg of active ingredient per hectare in order to achieve satisfying results. Sometimes, depending on the environmental conditions, the application rates may exceed the above designated limitations. However, the preferred application rates are between 0.05 kg and 1.0 kg a.i. per hectare.

As used in the foregoing definitions $C_1-C_5$alkyl denotes straight or branch chained saturated hydrocarbon radicals having from 1 to 5 carbon atoms, e.g. methyl, ethyl, propyl, 1-methylethyl, the four butyl isomers and the pentyl isomers; $C_1-C_7$alkyl includes $C_1-C_5$alkyl radicals and the higher homologs thereof having respectively 6 or 7 carbon atoms; $C_4-C_{13}$alkyl defines straight or branch chained saturated hydrocarbon radicals having from 4 to 13 carbon atoms, e.g. butyl, pentyl, hexyl, heptyl, octyl, nonyl, decyl, undecyl, dodecyl, tridecyl and their respective branched isomers; halo is fluoro, chloro, bromo or iodo, with fluoro and chloro being preferred; $C_3-C_5$alkenyl defines straight and branch chained hydrocarbon radicals containing one double bond and having friom 3 to 5 carbon atoms such as, for example, 2-propenyl, 3-butenyl, 2-butenyl, 2-pentenyl, 3-pentenyl, 2-methyl-2-propenyl or 3-methyl-2-butenyl, with 2-propenyl and 2-methyl-2-propenyl being preferred; $C_3-C_7$alkenyl includes $C_3-C_5$alkenyl radicals and the higher homologs thereof having respectively 6 or 7 carbon atoms; $C_3-C_5$alkynyl defines straight and branch chained hydrocarbon radicals containing one triple bond and having from 3 to 5 carbon atoms such as, for example, 2-propynyl, 2-butynyl, 3-butynyl, 2-pentynyl, 3-pentynyl or 4-pentynyl, with 2-propynyl being preferred; $C_3-C_7$alkynyl includes $C_3-C_5$alkynyl radicals and the higher homologs thereof having respectively 6 or 7 carbon atoms; and when said $C_3-C_7$alkenyl or said $C_3-C_7$alkynyl are substituted on a heteroatom, then the carbon atom of said $C_3-C_7$alkenyl or said $C_3-C_7$alkynyl connected to said heteroatom preferably is saturated; $C_3-C_7$cycloalkyl is generic to cyclopropyl, cyclobutyl, cyclopentyl, cyclohexyl and cycloheptyl, with cyclopentyl and cyclohexyl being preferred; $C_5-C_7$-cycloalkenyl is generic to cyclopentenyl, cyclohexenyl and cycloheptenyl.

As typical examples of $arylC_1-C_5$alkyl there may be mentioned phenylmethyl, phenylethyl, 4-chlorophenylmethyl, 4-chlorophenylethyl, 4-methoxyphenylmethyl or 3-methoxyphenylmethyl with phenylmethyl being preferred.

As examples of mono-, di- or trihalo$C_1-C_5$alkyl there may be mentioned fluoromethyl, difluoromethyl, trifluoromethyl, chloromethyl, trichloromethyl, 2,2,2-trifluoroethyl, 2,2,2-trichloroethyl and the like.

Depending on the nature of the moiety linked to the 1-position of the imidazole and/or the group L the compounds of formula (I) may contain asymmetrical carbon atoms. Unless otherwise mentioned or indicated, the chemical designation of compounds denotes the mixtures of all stereochemically isomeric forms. These mixtures contain all diastereomeres and enantiomers of the basic molecular structure.

Pure isomeric forms of these compounds can be separated from the mixtures by conventional separation methods. Preferably, if a specific stereochemical form is desired, said compound will be synthesized by stereoselective methods of preparation. These methods will advantageously employ optically active starting materials.

The invention also comprises the salt which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

Examples of salt-forming mineral acids are hydrofluoric acid, hydrochloric acid, hydrobromic acid, hydroiodic acid, sulfuric acid, nitric acid, chloric acid, perchloric acid or phosphoric acid. Preferred salt-forming sulfonic acids are toluenesulfonic acid, benzenesulfonic acid, methanesulfonic acid or trifluoromethanesulfonic acid. Preferred salt-forming carboxylic acids are acetic acid, trifluoroacetic acid, benzoic acid, chloroacetic acid, phthalic acid, maleic acid, malonic acid and citric acid. Phosphorus containing acids are the various phosphonous acids, phosphonic acids and phosphinic acids.

Preferred salt-forming alkali metal hydroxides and earth alkaline metal hydroxides are the hydroxides of lithium, sodium, potassium, magnesium or calcium, most preferably those of sodium or potassium. Example of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2.2.2]octane being most preferred. Examples of quaternary ammonium salts generally contain cations arising from ammonium hydroxides or ammonium halogenide salts, e.g. the tetramethylammonium, the trimethylphenylmethylammonium, the trieethylphenylmethylammonium, or the ammonium cation.

Preferred compounds within scope of the present invention are those compound of formula (I) wherein L is $—COOR^4$, cyano or a group $—C(=G)—D—R^6$; and/or $R^2$ is hydrogen, $C_1-C_7$alkyl, $C_3-C_7$alkenyl, $C_3-C_7$alkynyl, $C_5-C_7$cycloalkenyl, $C_3-C_7$cycloalkyl or mono-, di- or trihalo$C_{1-5}$alkyl; said $C_1-C_7$alkyl, $C_5-C_7$-cycloalkenyl or $C_3-C_7$cycloalkyl being optionally substituted with $C_1-C_5$alkyl; and/or $R^3$ is $C_4-C_{13}$alkyl, $C_5-C_7$cycloalkenyl or $C_3-C_7$cycloalkyl each optionally substituted with $C_1-C_5$alkyl.

Particularly preferred are those preferred compounds wherein D is $—N(R^7)—$ or $—N(R^8)—O—$; and/or $R^4$, $R^6$, $R^7$ and $R^8$ are hydrogen or $C_1-C_5$alkyl.

More particularly preferred compounds are those preferred or particularly preferred compounds wherein $R^1$ is hydrogen and/or $R^2$ is $C_1-C_7$alkyl or $C_3-C_7$cycloalkyl; and/or $R^3$ is $C_4-C_{13}$alkyl or $C_3-C_7$cycloalkyl.

As a preferred compound of this invention there may be mentioned methyl 1-(dicyclohexylmethyl)-1H-imidazole-5-carboxylate, the salts and stereoisomeric forms thereof.

The preparation of the compounds of formula (I) is generally carried out by the following methods.

The compounds of formula (I) can be obtained by condensing a compound of formula

(II)

wherein $R^2$, $R^3$ and L are as defined hereinabove, with a $C_1-C_4$alkyl ester of formic acid in the presence of suitable base such as, for example, an alkali metal alkoxide or hydride, e.g. sodium methoxide, potassium ethoxide, sodium hydride, lithium hydride, and the like, in a reaction-inert solvent; and treating the resultant intermediate of formula

(III)

wherein $R^2$, $R^3$ and L are as defined hereinabove and Z is an alkali metal atom, (a) with an alkali metal isothiocyanate in the presence of an acid, thus obtaining a 2-mercaptoimidazole of formula

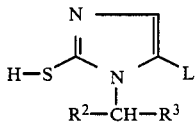

(I-a)

wherein $R^2$, $R^3$ and L are as defined hereinabove, which optionally is converted into a compound of formula

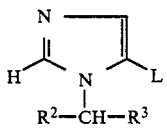

(I-b)

by reacting the starting compound (I-a) with nitric acid optionally in the presence of an alkali metal nitrite, e.g. sodium nitrite; or with Raney-nickel in the presence of a lower aliphatic alcohol, preferably ethanol, at a temperature between 40° C. and 80° C.; or also by treating the starting compounds with an aqueous hydrogen peroxide solution preferably in the presence of a carboxylic acid, e.g. acetic acid; or (b) with a carboxylic acid amide of 1 to 3 carbon atoms, preferably formamide, in the presence of an acid at a temperature between 50° C. and 250° C., preferably between 120° C. and 170° C.; or (c) with an excess of ammonium carbonate or hydrogen carbonate in a suitable solvent, which may be a reaction-inert solvent or an acid, at a temperature between 20° C. and 200° C., preferably between 25° C. and the reflux temperature of the reaction mixture.

In the afore-mentioned processes reaction-inert solvents are, for example, aromatic hydrocarbons such as benzene, methylbenzene or dimethylbenzene; ethers such as, for example, 1,1'-oxybisethane, tetrahydrofuran or 1,4-dioxane; or other aprotic organic solvents. For the cyclization-reaction of the imidazole ring structure, strong mineral acids such as hydrohalic acids, e.g. hydrochloric acid, are most conveniently employed. In the ring-forming variant (c) also other acids, e.g. acetic acid, can be used. In this reaction an excess of acid of 5 to 50, preferably of 15 to 40 times the required molar amount is most preferably used. The excess of ammonium salt in this process is 2 to 50, preferably 10 to 30 times the required molar amount.

The compounds of formula (I-b) can also be prepared by the deamination reaction of a 4-amino-1H-imidazole derivative of formula (IV), wherein L, $R^2$ and $R^3$ are as defined under formula (I) and L in particular is cyano, a group —COOR$^4$ or a radical —C(=G)—D—R$^6$ the latter more in particular being an amide group. Said deamination reaction involves a diazotation and a reductive dediazotation step which may be conducted sequentially, i.e. with isolation of the intermediate diazonium salt (IV-a) or in a one-pot fashion wherein said diazonium salt is reduced in situ.

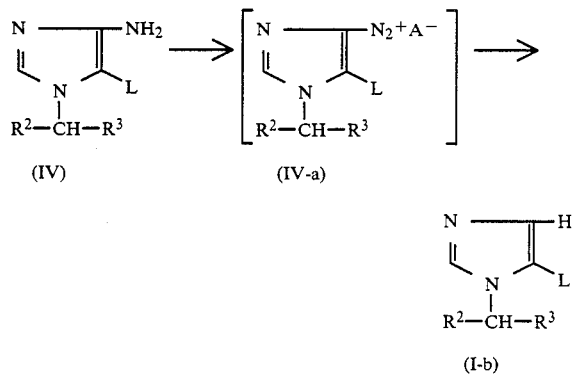

Treatment of the 4-amino-1H-imidazole derivative of formula (IV) in aqueous medium with an alkali metal nitrite, e.g. sodium or potassium nitrite, in the presence of an acid such as hydrochloric acid, sulfuric acid or nitric acid, or with nitronium tetrafluoroborate ($NO^+BF^-_4$) yields the diazonium salt (IV-a). In the latter, $A^-$ represents an anion corresponding to the conjugated base of the acid employed in the diazotation reaction or the tetrafluoroborate anion. The intermediate diazonium salts (IV-a) are reduced to the compounds of formula (I-b) by treatment with an appropriate reductant such as hypophosphoric acid at an elevated temperature, preferably at the boiling temperature of the reaction mixture.

Alternatively, treatment of the 4-amino-1H-imidazole derivatives of formula (IV) with a $C_{1-5}$alkyl nitrite such as, 1,1-dimethylethyl nitrite or 3-methylbutyl nitrite in suitable aprotic solvent such as tetrahydrofuran, 1,4-dioxane, trichloromethane or N,N-dimethylformamide yields a compound of formula (I-b) directly. The latter deamination reaction may conveniently be conducted at an elevated temperature, generally at the boiling point of the reaction mixture.

The compounds of formula (I) can also be converted into each other following art-known functional group transformation reactions. The substituent L on the imidazole ring may be transformed into other substituents encompassed by the definition of L by suitable reactions known in the art for the modification of carboxylic acid derivatives, e.g. by hydrolysis and esterification and/or transesterification and/or amidation or transamidation or conventional ring formation reactions.

The compounds of formula (I) wherein L is COOR$^4$ or C(=G)—D—R$^6$ can easily be obtained from the structurally related carboxylic acids or thiocarboxylic acids of formula (I) or functional derivatives thereof by amidation or esterification or from the related esters or amides by an appropriate transesterification or transamidation reaction. A preferred procedure is to transform the carboxylic acids into activated derivatives thereof, following art-known procedures, for example, by treating said acids with an appropriate halogenating reagent, such as, for example, thionyl chloride, thionyl bromide, phosphoryl chloride, phosphoryl bromide, phosphorous trichloride, phosphorous tribromide, pentachlorophosphorane and the like. Or by dehydrating the carboyxlic acid to the corresponding anhydride or by reacting the carboxylic acid with an acyl halide, e.g. acetyl or 2,2-dimethylpropanoyl chloride, ethyl or 1,1-dimethylethyl carbonochloridate and the like. The thus obtained activated derivatives of formula

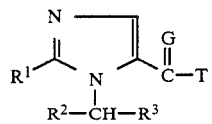

(V)

wherein $R^1$, $R^2$, $R^3$ and G are as defined under formula (I) and T is a reactive leaving group, e.g. halo, in particular chloro, bromo, —O—CO—O—$C_1$-$C_5$alkyl, —O—CO—$C_1$-$C_5$alkyl or a group

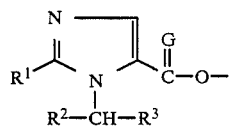

are reacted with an appropriate mercaptan or an amine of formula H—D—$R^6$, or with an alcohol of formula H—O—$R^4$. It may be appropriate to add a suitable base such as, for example, a trialkylamine. e.g. triethylamine to the reaction mixture in order to remove the acid which is liberated during the course of the reaction by salt-formation. Alternatively the compounds of formula (I) wherein L is a radical of formula —COOR$^4$ or —C(=G)—D—$R^6$ may also be prepared by treating the starting acids or thioacids and the amine, mercaptan or alcohol in the presence of a suitable reagent capable of forming amides, esters or thioesters, e.g. a carbodiimide such as dicyclohexylcarbodiimide (DCC), 2-halo-1-alkyl-pyridinium halides such as 2-chloro-1-methyl-pyridinium iodide, 1,1'-carbonylbis[1H-imidazole] and the like. The said amidation or esterification reactions are preferably conducted in a reaction-inert solvent such as, for example, a hydrocarbon, e.g. methylbenzene, dimethylbenzene; a halogenated hydrocarbon, e.g. dichloromethane, trichloromethane, an ether, e.g. tetrahydrofuran, dioxane; or a dipolar aprotic solvent, e.g. N,N-dimethylformamide, N,N-dimethylacetamide and the like solvents.

The compounds of formula (V) are novel compounds and as useful intermediates they constitute an additional feature of this invention.

The cyano compounds (L is —CN) may be obtained by dehydration of the corresponding aminocarbonyl compounds. Suitable dehydrating agents for this procedure known in the art are, for example, pentachlorophosphorane, phosphoryl chloride, thionyl chloride, phosphorus pentoxide, anhydrides such as acetic acid anhydride, trifluoroacetic acid anhydride and the like agents. The reaction temperature depends mainly on the nature of the chosen dehydrating agent but in general it is contemplated that the process can conveniently be carried out at temperatures comprised between room temperature and the boiling point of the reaction mixture in particular between +20° C. and +120° C. If desired, said dehydration reaction can be run in inert organic solvents such as, for example, a halogenated hydrocarbon, e.g. dichloromethane, trichloromethane, an ether, e.g. tetrahydrofuran, dioxane; or a polar aprotic solvent, e.g. N,N-dimethylformamide, N,N-dimethylacetamide and the like solvents.

The tetrazoles can be obtained by reacting the corresponding nitriles (L is —CN) with an alkali metal azide in a reaction inert organic solvent such as dimethyl formamide or dimethyl sulfoxide, at temperatures between +20° C. and +150° C.

The other heterocyclic compounds of formula I, wherein L is

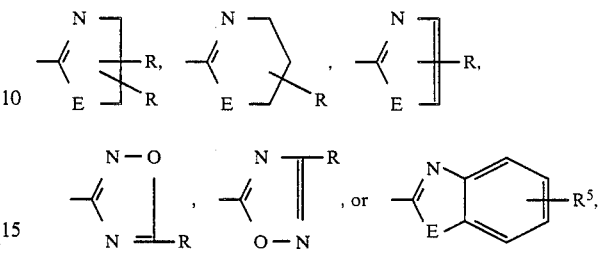

are synthesized by treatment of the corresponding carboxylic acids (L is —COOH) or derivatives thereof, for instance the acid halogenides, imino ethers, imino thioethers, amidines or amidoximes with reagents such as diamines, aminoalcohols, aminomercaptans, amidoximes, α-haloketones, α-haloaldehydes, acid halogenides or carboxylic acid anhydrides. Reactions of this type are known in the art. For example, general procedures are described in Chemistry of Carbon Compounds, Vol IV, Elsevier Publ. Co., 1957 in Heterocyclic Compounds, Wiley, N.Y., Vol. 5 (1957), Vol. 6 (1957), Vol. 7 (1961) and in the references cited therein.

The sulfur-containing compounds of formula (I) (L is —CS—D—$R^6$) can be produced by treating the corresponding oxygen-containing compounds of formula (I) (L is —CO—D—$R^6$) with phosphorous pentasulfide or with 2,4-bis(4-methoxyphenyl)-2,4-disulfide-1,3,2,4-dithiadiphosphetane (Lawesson's reagent). Preferentially, this reaction is carried out in the presence of a base and in an organic solvent such as N,N-dimethylformamide N,N-dimethylacetamide, hexamethylphosphoric triamide, acetonitrile, methylbenzene or dimethylbenzene.

The amidoximes of formula (I) (L is —C(NH$_2$)=N—O—R) can be obtained by reacting the nitriles (L is —CN) with hydroxylamine and optionally alkylating the resulting compound (L is —C(NH$_2$)=N—OH) by treatment with an alkylating agent.

The amidines of formula (I) [L is —C(=NR)—N-H—$R^6$] can be obtained by first converting a nitrile or nitrilium salt, prepared by treatment of the nitrile with $R_3O^+BF_4^-$, into an imino ether [L is —C(=N-R)—O—$C_1$-$C_5$alkyl] by reaction with a $C_1$-$C_5$alkanol in the presence of an acidic or basic catalyst and subsequently reacting the imino ether with an amine $R^6$—NH$_2$.

If the synthesis of stereochemically pure isomers is intended, stereoselective reaction steps and conditions are recommended. On the other hand conventional methods of separation can be used for obtaining pure isomers from a mixture of stereochemical isomers.

The starting materials for the preparation of the novel compounds of formula (I) are known or can be obtained by known synthesis procedures.

For example, the compounds of formula (II) can be obtained by reacting an amino methylene derivative of formula $$\begin{array}{c} H \diagdown \diagup CH_2-L \\ N \\ | \\ R^2-CH-R^3 \end{array} \quad (VI)$$

wherein $R^2$, $R^3$ and L are as defined hereinabove, with formic acid in the presence of acetic anhydride. In turn, the compounds of formula (VI) can be prepared by reacting an amine of formula $$\begin{array}{c} NH_2 \\ | \\ R^2-CH-R^3 \end{array} \quad (VII)$$

wherein $R^2$ and $R^3$ are as defined under formula (I), with a bromomethylene derivative of formula
Br—CH$_2$—L,     (VIII)

in the presence of an appropriate base such as sodium carbonate.

The 4amino-1H-imidazole derivatives of formula (IV) can be obtained by cyclizing an intermediate of formula $$\begin{array}{c} NC-N=CH-N-CH_2-L \\ | \\ R^2-CH-R^3 \end{array} \quad (IX)$$

under catalysis of a base at elevated temperature in a suitable solvent, e.g. an alcohol. A preferred mode of carrying out said cyclization may comprise the reaction of the starting compound (IX) in an alcohol, in the presence of a catalytic amount of alkoxide obtained by dissolving an alkali metal in said alcohol, at the boiling point of the reaction mixture. Or, alternatively, by reacting (IX) with an alkali metal alkoxide in a polar solvent such as N,N-dimethylformamide or dimethyl sulfoxide. Generally, the reaction temperatures are in the range of +60° C. to +140° C.

The intermediates of formula (IX) in turn can be prepared by alkylating an amidine of formula $$\begin{array}{c} NC-N=CH-NH-CH-R^2 \\ | \\ R^3 \end{array} \quad (X)$$

with a bromomethylene derivative of formula (VIII), in the presence of an appropriate base, such as, for example an alkali metal hydroxide, an alkali or earth alkaline metal carbonate or hydrogen carbonate, an earth alkaline oxide, an alkali metal alkoxide or a trialkylamine, e.g. sodium hydroxide, potassium hydroxide, sodium carbonate, potassium hydrogen carbonate, magnesium oxide, calcium oxide, sodium methoxide, sodium ethoxide, potassium ethoxide, potassium isopropoxide, pyridine, N,N-diethylethanamine and the like. In some instances, the addition of a crown-ether may be recoammendable. The reaction may conveniently be conducted at temperatures between +10° C. and the boiling point of the reaction mixture, either without a solvent or in a solvent such as N,N-dimethylformamide, N,N-dimethylacetamide or dimethyl sulfoxide.

The compounds of formula (X) can be prepared by reacting an amine of formula (VII) with a $C_{1-5}$alkyl-N-cyanomethanimidate of formula
$C_{1-5}$alkyl—O—CH=N—CN     (XI)

in an appropriate reaction-inert solvent such as trichloromethane, tetrahydrofuran, 1,4-dioxane, acetonitrile, N,N-dimethylformamide or N,N-dimethylacetamide. The said reaction can conveniently be carried out at temperatures between room temperature and the boiling point of the reaction mixture, in particular between +20° C. and +80° C. Removal of the $C_{1-5}$alkanol which is liberated during the course of the reaction and of the solvent by destillation under reduced pressure yields the N-cyanoamidine of formula (X) which in general need not be purified before further convertion.

The 4-amino-1H-imidazole derivatives of formula (IV) can alternatively be obtained from the amines of formula (VI), by a combined N-alkylating and cyclization reaction from the amines of formula (IV) in a one-step procedure in the same reaction vessel. The latter procedure is conducted in the same solvents and bases as mentioned hereinabove for the two step synthesis.

The amines of formula (VII) can be obtained by the reduction of an oxime of formula $$\begin{array}{c} N-OH \\ \| \\ R^2-C-R^3 \end{array} \quad (XII)$$

Said reduction is conveniently conducted with hydrogen in the presence of a noble metal catalyst or with a metallic hydride reagent, e.g. lithium tetrahydroaluminate or diborane in a suitable reaction-inert solvent such as an ether, e.g. tetrahydrofuran, 1,4-dioxane and the like. The oxime of formula (XII) may also be reduced electrochemically.

Said oxime (XII) in turn, can be prepared from the corresponding ketone of formula $$\begin{array}{c} O \\ \| \\ R^2-C-R^3 \end{array} \quad (XIII)$$

by reacting said ketone of formula (XIII) with hydroxylamine.

The amines of formula (VII) can also be prepared by the reductive amination of a ketone of formula (XIII) with formamide in the presence of formic acid and subsequent removal of the N-formyl group by treatment with a hydrohalic acid, e.g. hydrochloric acid.

The intermediates of formula (VI) can also be obtained by the reductive N-alkylation reaction of a ketone of formula (XIII) with an aminomethylene derivative (XIV).

$$(XIII) + H_2N-CH_2-L \xrightarrow{\text{reductive N-alkylation}} (VI)$$
$$(XIV)$$

Said reductive N-alkylation reaction may conveniently be carried out by hydrogenating a stirred and, if desired, heated mixture of the reactants in a suitable reaction-inert organic solvent according to art-known catalytic hydrogenating procedures. Suitable solvents are, for example, alkanols, e.g. methanol, ethanol; ethers, such as tetrahydrofuran. The term "art-known catalytic hydrogenating procedures" means that the reaction is carried out under hydrogen atmosphere and in the presence of a catalyst such as, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g. thiophene.

Alternatively, said reductive N-alkylation reactions may be conducted by treating a stirred and, if desired, heated mixture of the reactants with sodium cyanoborohydride, sodium borohydride, formic acid or a salt thereof, e.g. ammonium formiate.

The compounds of formula (I) are stable compounds and no precautionary measures are required for handling them.

When used at the indicated rates of application, the compounds of formula (I) have good selective herbicidal properties which make them most suitable for use in crops of useful plants, preferably in maize and in rice. In some cases damage is also caused to weeds which up to now have only been controlled with total herbicides.

At higher rates of application, all tested plants are so severely damaged in their development that they die.

The invention also relates to herbicidal compositions containing one or more inert carriers and, if desired, other adjuvants and as active ingredient a herbicidally effective amount of a compound of formula (I) as defined hereinabove. Further the invention relates to a method of controlling weeds, said method comprising applying to said weeds or to the locus thereof of a herbicidally effective amount of a compound of formula (I) as defined hereinabove.

In the method for controlling weeds according to the invention the compounds of formula (I) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. The nature of the compositions and the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared by known means, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or N,N-dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula (I) to be formulated, suitable surface-active compounds are non-ionic, cationic and/or anionic surfactants having good emulsifying, dispersing and wetting porperties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, earth alkaline metal salts or unsubstituted or substituted ammonium salts and contain an alkyl radical having from 8 to 22 carbon atoms, which also includes the alkyl moiety derived from acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., New York, 1980–81.

The herbicidal compositions which are preferably employed in the method of the invention usually contain 0.1 to 95%, preferably 0.1 to 80%, of a compound of formula (I), 1 to 99.9%, of a solid or liquid adjuvant, and 0 to 25%, preferably 0.1 to 25%, of a surfactant.

Preferred formulations are composed in particular of the following constituents (%=percentage by weight):

Emulsifiable concentrates

| active ingredient: | 1 to 20%, preferably 5 to 10% |
| --- | --- |
| surfactant: | 5 to 30%, preferably 10 to 20% |
| liquid carrier: | 50 to 94%, preferably 70 to 85% |

Dusts

| active ingredient: | 0.1 to 10%, preferably 0.1 to 1% |
| --- | --- |
| solid carrier: | 99.9 to 90%, preferably 99.9 to 99% |

Suspension concentrates

| active ingredient: | 5 to 75%, preferably 10 to 50% |
| --- | --- |
| water: | 94 to 25%, preferably 88 to 30% |
| surfactant: | 1 to 40%, preferably 2 to 30% |

Wettable powders

| active ingredient: | 0.5 to 90%, preferably 1 to 80% |
| --- | --- |
| surfactant: | 0.5 to 20%, preferably 1 to 15% |
| solid carrier: | 5 to 95%, preferably 15 to 90% |

Granulates

| active ingredient: | 0.5 to 30%, preferably 3 to 15% |
| --- | --- |
| solid carrier: | 99.5 to 70%, preferably 97 to 85% |

The following examples are intended to illustrate and not to limit the scope of the present invention. Unless otherwise stated all parts therein are by weight.

EXPERIMENTAL PART

A. Preparation of Intermediates

Example 1

(a) 111 Parts of α-cyclohexylcyclohexanemethanamine and 60 parts of sodium carbonate were dispersed in 320 parts of methanol. 54 Parts of methyl bromoacetate were added dropwise to this dispersion. The mixture was stirred at room temperature for 72 hours. The precicitate was separated and the solution was concentrated to dryness, yielding methyl N-[(dicyclohexyl)methyl]glycine quantitatively (int. 1).

(b) 143 Parts of methyl N-[(dicyclohexyl)methyl]glycine were added dropwise to 290 parts of formic acid while cooling to 5° C. Subsequently 90 parts of acetic anhydride were added, and the mixture was kept at room temperature for 48 hours. Destillation under vacuo afforded 154 parts of methyl N-[(dicyclohexyl)methyl]-N-formylglycine (int. 2).

Example 2

(a) A mixture of 130 parts of 1-cyclohexyl-1-butanone, 225 parts of methyl glycine, 2 parts of a solution of thiophene in methanol 4%, 960 parts of methanol and 200 parts of potassium acetate was hydrogenated overnight in a Parr apparatus with 5 parts of palladium-on-charcoal catalyst 10%. After the calculated amount of hydrogen was taken up, the catalyst was filtered off and the filtrate was evaporated. The residue was taken up in water and 1,1'-oxybisethane. The whole was extracted with a hydrochloric acid solution 10%. The aqueous layer was treated with a sodium hydroxide solution and the product was extracted with 1,1'-oxybisethane. The extract was dried, filtered and evaporated, yielding 46 parts (22.4%) of methyl N-(1-cyclohexylbutyl)glycine as a residue (int. 3).

(b) A solution of 45 parts of methyl N-(1-cyclohexylbutyl)glycine in 50 parts of acetic acid, anhydride and 300 parts of formic acid was stirred for 14 hours at room temperature. The reaction mixture was evaporated and the residue was taken up in dichloromethane. The organic layer was washed with water and a sodium carbonate solution, dried, filtered and evaporated. The residue was crystallized from a mixture of 2,2'-oxybispropane and petroleum ether. The product was filtered off and dried, yielding 48 parts (94.9%) of methyl N-(1-cyclohexylbutyl)-N-formylglycine as a residue (int. 4).

Other intermediates are either known or can be obtained by analogous methods of preparation.

B. Preparation of Final compounds

Example 3

A solution of 30 parts of sodium methoxide in 720 parts of tetrahydrofuran was prepared by adding suitable amounts of methanol and sodium hydride to the tetrahydrofuran. With optional cooling to room temperature 94 parts of methyl formate and methyl N-[(dicyclohexyl)methyl]-N-formylglycine were added. After 22 hours the mixture was taken up with 280 parts of deionisized water and 2.6 parts of hexane. The aqueous phase was separated, and 225 parts of methanol and 140 parts of 36% hydrochloric acid were added. The solution was heated to 40°–50° C. and treated with a solution of 82 parts of potassium thiocyanate in 160 parts of deionisized water. The mixture was stirred at room temperature for 18 hours. During this period 67 parts of methyl 1-[(dicyclohexyl)methyl]-2-mercapto-1H-imidazole-5-carboxylate precipitate. After recrystallisation from methanol the product had a melting point of 217° C. (dec.) (compound 1).

Example 4

2.8 Parts of sodium nitrite and 33 parts of nitric acid were solved in 250 parts of deionisized water. Within 1 hour 46 parts of methyl 1-[(dicyclohexyl)methyl]-2-mercapto-1H-imidazole-5-carboxylate were added portionwise at a temperature between 30° C. and 45° C. The precipitate was isolated affording the nitric acid addition salt of methyl 1-[(dicyclohexyl)methyl]-1H-imidazole-5-carboxylate; mp. 194.5° C. (dec.) (compound 2). This salt was treated with 10% aqueous sodium carbonate. Extracting the aqueous phase with trichloromethane, and evaporating the organic solvent yields 24.5 parts of methyl 1-[(dicyclohexyl)methyl]-1H-imidazole-5-carboxylate as a colourless product, mp. 104°–105° C. (compound 3).

Example 5

A mixture of 6 parts methyl 1-[(dicyclohexyl)methyl]-1H-imidazol-5-carboxylate, 6 parts of a sodium hydroxide solution 50% and 100 parts of water is stirred for 2 hours at reflux temperature. The reaction mixture is acidified with concentrated hydrochloric acid and the product is extracted with trichloromethane. The extract is dried, filtered and evaporated. The residue is boiled for 2 hours in acetonitrile. The precipitated product is filtered off and dried, yielding 1-[(dicyclohexyl)methyl]-1H-imidazole-5-carboxylic acid; mp. 253° C. (compound 4).

Example 6

To a stirred solution of 49 parts of methyl N-(1-cyclohexylbutyl)-N-formylglycine in 225 parts of tetrahydrofuran were added 9.8 parts of a sodium hydride dispersion 50%. After stirring for 15 minutes at room temperature, 40 parts of methyl formate were added. The whole was stirred overnight at room temperature. The mixture was evaporated and the residue was stirred in a mixture of 300 parts of water and 210 parts of 1,1'-oxybisethane. The aqueous layer was acidified and the product was extracted with dichloromethane. The extract was dried, filtered and evaporated. The residue was dissolved in 120 parts of methanol and treated with 40 parts of hydrochloric acid, 40 parts of potassium thiocyanate and 100 parts of water. After stirring overnight at 50° C., 200 parts of water were added. The precipitated product was filtered off and dried in vacuo, yielding 33.4 parts (56.3%) of methyl 1-(1-cyclohexylbutyl)-2-mercapto-1H-imidazole-5-carboxylate; mp. 181.4° C. (compound 25).

Example 7

A solution of 30 parts of methyl 1-(1-cyclohexylbutyl)-2-mercapto-1H-imidazole-5-carboxylate in 150 parts of concentrated nitric acid and 100 parts of water was stirred for 1 hour at room temperature (intense reaction). The whole was cooled in crushed ice and treated with a sodium hydroxide solution. The product was extracted with 1,1'-oxybisethane. The extract was washed twice with water, dried, filtered and evaporated. The residue was converted into the nitrate salt in 2,2'-oxybispropane. The salt was filtered off and dried, yielding 27 parts (82.4%) of methyl 1-(1-cyclohexylbutyl)-1H-imidazole-5-carboxylate mononitrate; mp. 128.9° C. (compound 26).

Example 8

A solution of 24 parts of methyl 1-(1-cyclohexylbutyl)-1H-imidazole-5-carboxylate in 50 parts of a sodium hydroxide solution 50% and 50 parts of water was stirred for 1.5 hours at reflux temperature. After cooling, the mixture was poured into 500 parts of water and the whole was neutralized with concentrated hydrochloric acid. The precipitated product was filtered off and dried, yielding 12.8 parts (64.7%) of 1-(1-cyclohexylbutyl)-1H-imidazole-5-carboxylic acid; mp. 201.7° C. (compound 27).

Example 9

To a stirred solution of 8.7 parts of 1-(1-cyclohexylbutyl)-1H-imidazole-5-carboxylic acid in 45 parts of tetrahydrofuran were added portionwise 5.7 parts of 1,1'-carbonylbis[1H-imidazole]. Upon complete addition, stirring was continued for 1 hour at room temperature. Two portions of 9 parts of a methanamine solution 40% in water were added and after stirring for 1 hour at room temperature, the mixture was evaporated. The residue was taken up in 1,1'-oxybisethane. The organic layer was washed three times with water, dried, filtered and evaporated. The residue was converted into the nitrate salt in 2,2'-oxybispropane. The salt was filtered off and dried, yielding 4.8 parts (42.0%) of 1-(1-cyclohexylbutyl)-N-methyl-1H-imidazole-5-carboxamide mononitrate; mp. 181.1° C. (compound 28).

The other compounds listed in Table 1 can be obtained by analogous methods of preparation.

TABLE 1

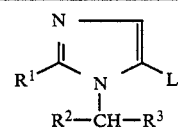

| No. | R¹ | L | R² | R³ | physical data |
|---|---|---|---|---|---|
| 1 | SH | —COOCH₃ | c-C₆H₁₁ | c-C₆H₁₁ | mp. 217° C. (dec) |
| 2 | H | —COOCH₃ | c-C₆H₁₁ | c-C₆H₁₁ | HNO₃/mp. 194.5° C. |
| 3 | H | —COOCH₃ | c-C₆H₁₁ | c-C₆H₁₁ | mp. 104°–105° C. |
| 4 | H | —COOH | c-C₆H₁₁ | c-C₆H₁₁ | mp. 253° C. |
| 5 | H | —CO—NH—CH₃ | c-C₆H₁₁ | c-C₆H₁₁ | |
| 6 | H | —COOC₂H₅ | c-C₆H₁₁ | c-C₆H₁₁ | |
| 7 | H | —COO—C₃H₇—n | c-C₆H₁₁ | c-C₆H₁₁ | |
| 8 | H | —COO—C₄H₉—n | c-C₆H₁₁ | c-C₆H₁₁ | |
| 9 | H | —COO—cyclohexyl | c-C₆H₁₁ | c-C₆H₁₁ | |
| 10 | H | —COOCH₂—CH═CH₂ | c-C₆H₁₁ | c-C₆H₁₁ | |
| 11 | H | —COO—CH₂—C≡CH | c-C₆H₁₁ | c-C₆H₁₁ | |
| 12 | H | —COO—CH₂C₆H₅ | c-C₆H₁₁ | c-C₆H₁₁ | |
| 13 | H | —COO—CH₂O—CH₃ | c-C₆H₁₁ | c-C₆H₁₁ | |
| 14 | H | —CO—NH—C₂H₅ | c-C₆H₁₁ | c-C₆H₁₁ | |
| 15 | H | —CO—NH—C₃H₇—n | c-C₆H₁₁ | c-C₆H₁₁ | |
| 16 | H | —CO—NH—C₄H₉—n | c-C₆H₁₁ | c-C₆H₁₁ | |

TABLE 1-continued

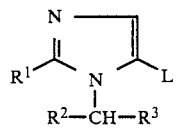

| No. | R¹ | L | R² | R³ | physical data |
|---|---|---|---|---|---|
| 17 | H | $-CO-NH_2$ | $c\text{-}C_6H_{11}$ | $c\text{-}C_6H_{11}$ | |
| 18 | H | $-COO-NH-OCH_3$ | $c\text{-}C_6H_{11}$ | $c\text{-}C_6H_{11}$ | |
| 19 | H | $-CO-NH-C_3H_5\text{-}c$ | $c\text{-}C_6H_{11}$ | $c\text{-}C_6H_{11}$ | |
| 20 | H | $-CO-S-CH_3$ | $c\text{-}C_6H_{11}$ | $c\text{-}C_6H_{11}$ | |
| 21 | H | $-CO-NH-NH_2$ | $c\text{-}C_6H_{11}$ | $c\text{-}C_6H_{11}$ | |
| 22 | H | $-CO-NH-NH-CH_3$ | $c\text{-}C_6H_{11}$ | $c\text{-}C_6H_{11}$ | |
| 23 | H | $-CO-$1-pyrrolidinyl | $c\text{-}C_6H_{11}$ | $c\text{-}C_6H_{11}$ | |
| 24 | H | $-C\equiv N$ | $c\text{-}C_6H_{11}$ | $c\text{-}C_6H_{11}$ | |
| 25 | SH | $-COOCH_3$ | $n\text{-}C_3H_7$ | $c\text{-}C_6H_{11}$ | mp. 181.4° C. |
| 26 | H | $-COOCH_3$ | $n\text{-}C_3H_7$ | $c\text{-}C_6H_{11}$ | $HNO_3$/mp. 128.9° C. |
| 27 | H | $-COOH$ | $n\text{-}C_3H_7$ | $c\text{-}C_6H_{11}$ | mp. 201.7° C. |
| 28 | H | $-CO-NH-CH_3$ | $n\text{-}C_3H_7$ | $c\text{-}C_6H_{11}$ | $HNO_3$/mp. 181.1° C. |
| 29 | SH | $-COOCH_3$ | $i\text{-}C_3H_7$ | $c\text{-}C_6H_{11}$ | |
| 30 | H | $-COOCH_3$ | $i\text{-}C_3H_7$ | $c\text{-}C_6H_{11}$ | $HNO_3$ |
| 31 | H | $-CO-NH-CH_3$ | $i\text{-}C_3H_7$ | $c\text{-}C_6H_{11}$ | |
| 32 | H | $-COOH$ | $i\text{-}C_3H_7$ | $c\text{-}C_6H_{11}$ | |
| 33 | SH | $-COOCH_3$ | $c\text{-}C_5H_9$ | $c\text{-}C_6H_{11}$ | |
| 34 | H | $-COOCH_3$ | $c\text{-}C_5H_9$ | $c\text{-}C_6H_{11}$ | $HNO_3$ |
| 35 | H | $-CO-NH-CH_3$ | $c\text{-}C_5H_9$ | $c\text{-}C_6H_{11}$ | |
| 36 | H | $-COOH$ | $c\text{-}C_5H_9$ | $c\text{-}C_6H_{11}$ | |
| 37 | SH | $-COOCH_3$ | $c\text{-}C_5H_9$ | $c\text{-}C_5H_9$ | |
| 38 | H | $-COOCH_3$ | $c\text{-}C_5H_9$ | $c\text{-}C_5H_9$ | $HNO_3$ |
| 39 | H | $-CO-NH-CH_3$ | $c\text{-}C_5H_9$ | $c\text{-}C_5H_9$ | |
| 40 | H | $-COOH$ | $c\text{-}C_5H_9$ | $c\text{-}C_5H_9$ | |
| 41 | SH | $-COOCH_3$ | 1-cyclohexenyl | $c\text{-}C_6H_{11}$ | |
| 42 | H | $-COOCH_3$ | 1-cyclohexenyl | $c\text{-}C_6H_{11}$ | $HNO_3$ |
| 43 | H | $-COOCH_3$ | 1-cyclohexenyl | $c\text{-}C_6H_{11}$ | |
| 44 | H | $-COOH$ | 1-cyclohexenyl | $c\text{-}C_6H_{11}$ | |
| 45 | H | $-CO-NH-CH_3$ | 1-cyclohexenyl | $c\text{-}C_6H_{11}$ | |
| 46 | SH | $-COOCH_3$ | $n\text{-}C_9H_{19}$ | $c\text{-}C_9H_{19}$ | mp. 76.2° C. |
| 47 | H | $-COOCH_3$ | $n\text{-}C_9H_{19}$ | $n\text{-}C_9H_{19}$ | $HNO_3$ |
| 48 | H | $-COOCH_3$ | $n\text{-}C_9H_{19}$ | $n\text{-}C_9H_{19}$ | mp. 47.5° C. |
| 49 | H | $-COOH$ | $n\text{-}C_9H_{19}$ | $n\text{-}C_9H_{19}$ | |
| 50 | H | $-CO-NH-CH_3$ | $n\text{-}C_9H_{19}$ | $n\text{-}C_9H_{19}$ | |
| 51 | SH | $-COOCH_3$ | $CH_3$ | $c\text{-}C_6H_{11}$ | |
| 52 | H | $-COOCH_3$ | $CH_3$ | $c\text{-}C_6H_{11}$ | |
| 53 | SH | $-COOCH_3$ | $C_2H_5$ | $c\text{-}C_6H_{11}$ | |
| 54 | H | $-COOCH_3$ | $C_2H_5$ | $c\text{-}C_6H_{11}$ | |
| 55 | SH | $-COOCH_3$ | $c\text{-}C_6H_{11}$ | $c\text{-}C_3H_5$ | |
| 56 | H | $-COOCH_3$ | $c\text{-}C_6H_{11}$ | $c\text{-}C_3H_5$ | |
| 57 | SH | $-COOCH_3$ | $c\text{-}C_5H_9$ | $c\text{-}C_3H_5$ | |
| 58 | H | $-COOCH_3$ | $c\text{-}C_5H_9$ | $c\text{-}C_3H_5$ | |
| 59 | SH | $-COOCH_3$ | H | $n\text{-}C_{17}H_{35}$ | |
| 60 | H | $-COOCH_3$ | H | $n\text{-}C_{17}H_{35}$ | |
| 61 | SH | $-COOCH_3$ | $CH_2CH=CH_2$ | $c\text{-}C_6H_{11}$ | |
| 62 | H | $-COOCH_3$ | $CH_2CH=CH_2$ | $c\text{-}C_6H_{11}$ | |
| 63 | SH | $-COOCH_3$ | $C_4H_9-n$ | $C_4H_9-n$ | mp. 122.8° C. |
| 64 | H | $-COOCH_3$ | $C_4H_9-n$ | $C_4H_9-n$ | $HNO_3$/mp. 109.8° C. |
| 65 | H | $-COOH$ | $C_4H_9-n$ | $C_4H_9-n$ | mp. 181.3° C. |
| 66 | H | $-CO-NH-CH_3$ | $C_4H_9-n$ | $C_4H_9-n$ | mp. 92.9° C. |
| 67 | H | $-COOCH_2CH_3$ | $C_4H_9-n$ | $C_4H_9-n$ | oil |
| 68 | SH | $-COOCH_3$ | $C_2H_5$ | $C_5H_{11}-n$ | — |
| 69 | H | $-COOCH_3$ | $C_2H_5$ | $C_5H_{11}-n$ | oil |
| 70 | H | $-COOH$ | $C_2H_5$ | $C_5H_{11}-n$ | mp. 142.9° C. |
| 71 | H | $-CO-NH-CH_3$ | $C_2H_5$ | $C_5H_{11}-n$ | $HNO_3$/mp. 133.7° C. |
| 72 | SH | $-COOCH_3$ | $C_5H_{11}-n$ | $C_5H_{11}-n$ | solid |
| 73 | H | $-COOCH_3$ | $C_5H_{11}-n$ | $C_5H_{11}-n$ | oil |

(C) COMPOSITION EXAMPLES

Example 10: Composition examples for solid compounds of formula (I) (percentages are by weight)

| (a) Wettable powders | (a) | (b) | (c) |
|---|---|---|---|
| compound of formula (I) | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredient was thoroughly mixed with the adjuvants and the mixture was thoroughly ground in a suitable mill, affording wettable powders which could be diluted with water to give suspensions of the desired concentration.

| (b) Emulsifiable concentrate | (a) | (b) |
|---|---|---|
| compound of formula (I) | 10% | 1% |
| octylphenol polyethylene glycol ether (4-5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| dimethylbenzene mixture | 50% | 79% |

Emulsions of any required concentration could be obtained from this concentrate by dilution with water.

| (c) Dusts | (a) | (b) |
|---|---|---|
| compound of formula (I) | 0.1% | 1% |
| talcum | 99.9% | — |
| kaolin | — | 99% |

Usable dusts were obtained by mixing the active ingredient with the carriers, and grinding the mixture in a suitable mill.

| (d) Extruder granulate | (a) | (b) |
|---|---|---|
| compound of formula (I) | 10% | 1% |
| sodium lignosulfate | 2% | 2% |
| carboxymethylcellulose | 1% | 1% |
| kaolin | 87% | 96% |

The active ingredient was mixed and ground with the adjuvants, and the mixture was subsequently moistened with water. The mixture was extruded and dried in a stream of air.

| (e) Coated granulate | | |
|---|---|---|
| compound of formula (I) | | 3% |
| polyethylene glycol (mol. wt. 200) | | 2% |
| kaolin | | 95% |

The finely ground active ingredient was uniformly applied, in a mixer, to the kaolin moistened with polyethylene glycol. Non-dusty coated granulates were obtained in this manner.

| (f) Suspension concentrate | (a) | (b) |
|---|---|---|
| compound of formula (I) | 40% | 5% |
| ethylene glycol | 10% | 10% |
| nonylphenol polyethylene glycol ether (15 moles of ethylene oxide) | 6% | 1% |
| sodium lignosulfate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient was intimately mixed with the adjuvants, giving a suspension concentrate from which suspension of any desired concentration could be obtained by dilution with water.

| (g) Salt solution | | |
|---|---|---|
| compound of formula (I) | | 5% |
| isopropylamine | | 1% |
| octylphenol polyethylene glycol ether (78 moles of ethylene oxide) | | 3% |
| water | | 91% |

Example 11: Composition examples for liquid active ingredients of formula (I) (throughout, percentages are by weight)

| (a) Emulsifiable concentrates | (a) | (b) | (c) |
|---|---|---|---|
| compound of formula (I) | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cylohexanone | — | 15% | 20% |
| dimethylbenzene mixture | 70% | 25% | 20% |

Emulsions of any required concentration could be produced from such concentrate by dilution with water.

| (b) Solutions | (a) | (b) | (c) | (d) |
|---|---|---|---|---|
| compound of formula (I) | 80% | 10% | 5% | 95% |
| ethylene glycol monoethyl ether | 20% | — | — | — |
| polyethylene glycol (MG 400) | — | 70% | — | — |
| N—methyl-2-pyrrolidone | — | 20% | — | — |
| epoxidised coconut oil | — | — | 1% | 5% |
| petroleum distillate (boiling range 160-190° C.) | — | — | 94% | — |

These solutions were suitable for application in the form of microdrops.

| (c) Granulates | (a) | (b) |
|---|---|---|
| compound of formula (I) | 5% | 10% |
| kaolin | 94% | — |
| highly dispersed silicic acid | 1% | — |
| attapulgite | — | 90% |

The active ingredient was dissolved in methylene chloride, the solution was sprayed onto the carrier, and the solvent was subsequently evaporated off in vacuo.

| (d) Dusts | (a) | (b) |
|---|---|---|
| compound of formula (I) | 2% | 5% |
| highly dispersed silicic acid | 1% | 5% |
| talcum | 97% | — |
| kaolin | — | 90% |

Ready-for-use dusts were obtained by intimately mixing the carriers with the active ingredient.

(D) BIOLOGICAL EXAMPLES

Example 12: Preemergence herbicidal action

In a greenhouse, immediately after sowing the test plants in seed dishes, the surface of the soil was treated with an aqueous dispersion of the test compounds, obtained from a 25% emulsifiable concentrate or from a 25% wettable powder with test compounds, which on account of their insufficient solubility could not be formulated to emulsifiable concentrates. Three different concentration series were used, corresponding to 4,2 and 1 kg of test compound per hectare respectively. The seed dishes were kept in the greenhouse at 22°-25°

C. and 50-70% relative humidity. The test was evaluated 3 weeks later in accordance with the following rating:

1 = plants had not germinated or were totally withered
2-3 = very strong action
4-6 = average action
7-8 = slight action
9 = no action Results: Preemergence test

|  | dosage kg a.i./ha | | | | | |
|---|---|---|---|---|---|---|
|  | Comp. 1 | | | Comp. 2 | | |
| plant tested | 4 | 2 | 1 | 4 | 2 | 1 |
| soja | 9 | 9 | 9 | 9 | 9 | 9 |
| maize | 9 | 9 | 9 | 9 | 9 | 9 |
| alopecurus myos. | 2 | 3 | 4 | 1 | 1 | 4 |
| digitaria sang. | 1 | 2 | 3 | 1 | 1 | 2 |
| echinochloa c.g. | 1 | 2 | 4 | 1 | 1 | 2 |
| sida spinosa | 2 | 3 | 7 | 3 | 4 | 7 |
| amaranthus ret. | 2 | 2 | 8 | 2 | 2 | 4 |
| chenopodium sp. | 4 | 7 | 9 | 3 | 4 | 7 |
| solanum nigrum | 2 | 2 | 4 | 2 | 2 | 8 |
| chrysanthe. leuc. | 5 | 6 | 9 | 4 | 5 | 7 |
| galium aparine | 4 | 6 | 8 | 4 | 5 | 6 |
| viola tricolor | 2 | 2 | 2 | 2 | 2 | 3 |
| veronica sp. | 1 | 1 | 2 | 2 | 2 | 2 |

Example 13: Postemergence herbicidal action (Contact herbicide)

A number of weeds were sprayed postemergence in the 4- to 6-leaf stage with an aqueous active ingredient dispersion in rates of 4 kg of test compound per hectare and kept at 24°-26° C. and 45-60% relative humidity. The test was evaluated at least 15 days after treatment in accordance with the same rating as employed in the preemergence test.

Results: dosage 4 kg active ingredient per hectare

| compound | plant tested | | |
|---|---|---|---|
| tested | solanum | sinapis | phaseolus |
| 3 | 4 | 4 | 3 |
| 26 | 1 | 1 | 2 |
| 63 | 3 | 3 | 3 |
| 64 | 2 | 1 | 2 |
| 66 | 2 | 2 | 2 |

Example 14: Herbicidal action in transplanted rice crops 25 days old rice shoots of the variety "Yamabiko" were transplanted into large plastic containers. Into the same containers seeds of the weeds occuring in rice crops, namely echinochloa, scirpus and monochoria were sown between the rice plants. The containers were watered to such an extent, that a water layer of 2.5 cm covered the surface. After 3 days under greenhouse conditions, the diluted aqueous dispersions of the active compounds were added to the water layer at a rate of application of 1000, 500, 250 and 125 g a.i. per hectare. The containers were then kept covered with water at a temperature 25° C. and high humidity in a greenhouse for 4 weeks. The evaluation of the tests was made in accordance with the rating given in Example 13.

Results:

|  | Compound No. | | | | | | | |
|---|---|---|---|---|---|---|---|---|
|  | 1 | | | | 2 | | | |
|  | in g a.i. per hectare | | | | in g a.i. per hectare | | | |
| Tested plant | 1000 | 500 | 250 | 125 | 1000 | 500 | 250 | 125 |
| rice "Yamabiko" | 8 | 9 | 9 | 9 | 7 | 9 | 9 | 9 |
| echinochloa c.g. | 2 | 3 | 4 | 5 | 1 | 1 | 1 | 3 |
| scirpus | 1 | 1 | 2 | 4 | 1 | 1 | 1 | 5 |
| monochoria | 1 | 1 | 1 | 3 | 1 | 1 | 1 | 2 |

Example 15: Herbicidal action against waterweeds

The seeds of the waterweeds Echinochloa crus galli and Monochoria vaginalis were sown in plastic containers (60 cm² surface, 500 ml by volume) together. The containers were watered up to the soil surface and after three days the water level was raised slightly above the soil surface (3-5 mm). Three days after sowing an aqueous emulsion of the active compound was applied by spraying the containers at a rate of application of 4 kg of a.i. per hectare (dilution 550 l/ha). The containers were kept in a greenhouse for three weeks under conditions optimal for the waterweeds, i.e. at a temperature between 20° and 25° C. and under high humidity.

The evaluation of the tests was made in accordance with the rating given in example 12.

Results: dosage 4 kg active ingredient per hectare

| compound | plant tested | |
|---|---|---|
| tested | Echinochloa | Monochoria |
| 2 | 1 | 1 |
| 3 | 1 | 1 |
| 25 | 4 | 1 |
| 26 | 1 | 1 |
| 28 | 1 | 1 |
| 64 | 2 | 1 |
| 66 | 1 | 1 |

We claim:

1. A chemical compound having the formula

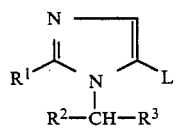

(I)

or a stereoisomeric form thereof, or a salt thereof, wherein $R^1$ is hydrogen or mercapto;

$R^2$ is hydrogen, $C_1$-$C_7$alkyl, $C_3$-$C_7$alkenyl, $C_3$-$C_7$alkynyl, $C_3$-$C_7$cycloalkyl, $C_5$-$C_7$cycloalkenyl; said $C_1$-$C_7$alkyl, $C_3$-$C_7$alkenyl, $C_3$-$C_7$alkynyl, $C_3$-$C_7$cycloalkyl, $C_5$-$C_7$cycloalkenyl being optionally substituted with one to three radicals selected from $C_1$-$C_5$alkyl, $C_1$-$C_5$alkyloxy, hydroxy$C_1$-$C_5$alkyl, $C_1$-$C_5$alkyloxy$C_1$-$C_5$alkyl and halo;

$R^3$ is $C_4$-$C_{13}$alkyl, $C_3$-$C_7$cycloalkyl, or $C_5$-$C_7$cycloalkenyl each unsubstituted or substituted with one to three radicals selected from $C_1$-$C_5$alkyl, $C_1$-$C_5$alkyloxy, hydroxy$C_1$-$C_5$alkyl, $C_1$-$C_5$alkyloxy$C_1$-$C_5$alkyl and halo;

L is cyano, —COOR⁴,

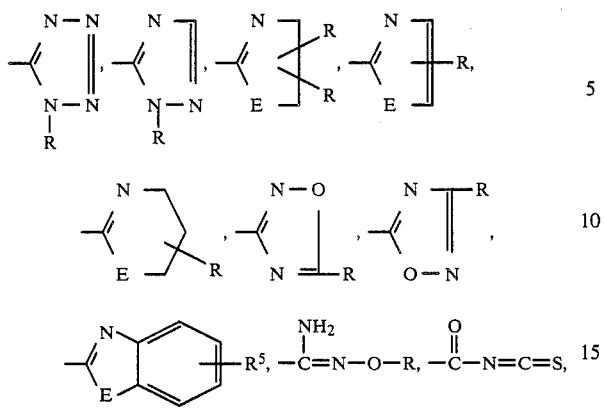

or a group of —C(=G)—D—R$^6$;

R$^4$ is hydrogen, C$_1$–C$_7$alkyl, mono-, di- or trihaloC$_1$–C$_5$alkyl, C$_3$–C$_7$alkenyl, C$_3$–C$_7$alkynyl, C$_3$–C$_7$cycloalkyl, C$_1$–C$_7$alkyloxyC$_1$–C$_7$alkyl or arylC$_1$–C$_5$alkyl;

E is oxygen, sulfur or —NR—;
R is hydrogen or C$_1$–C$_5$alkyl;
G is =N—R, oxygen or sulfur;
D is sulfur, —N(R$^7$)—, —N(R$^8$)—NH—, —N(R$^8$)—O—,

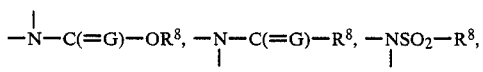

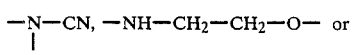

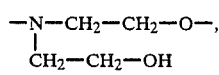

R$^6$, R$^7$ and R$^8$ are independently selected from hydrogen, C$_1$–C$_5$alkyl, C$_3$–C$_5$alkenyl, C$_3$–C$_5$alkynyl, C$_3$–C$_7$cycloalkyl or C$_1$–C$_5$alkyl substituted with aryl, C$_3$–C$_7$cycloalkyl, C$_3$–C$_7$cycloalkyloxy, C$_1$–C$_5$alkyloxy, hydroxy, carboxyl or C$_1$–C$_5$alkyloxycarbonyl; whereas R$^8$ may also be aryl; or R$^6$ and R$^7$ together with the nitrogen atom to which they are attached may form a piperidinyl, pyrrolidinyl, 2-oxopiperidinyl, 2-oxopyrrolidinyl, morpholinyl, thiomorpholinyl, piperazinyl or 4-(C$_1$–C$_5$alkyl)piperazinyl ring, each unsubstituted or substituted with one to three C$_1$–C$_5$alkyl groups;

R$^5$ is hydrogen, C$_1$–C$_5$alkyl, C$_1$–C$_5$alkyloxy, halo, trifluoromethyl, difluoromethoxy, cyano, nitro, amino, mono- and diC$_1$–C$_5$alkylamino or C$_1$–C$_5$alkylcarbonylamino; and aryl is phenyl optionally substituted with one to three substituents each independently selected from C$_1$–C$_5$alkyl, C$_1$–C$_5$alkyloxy and halo provided that R$^4$ is other than methyl when R$^2$ is hydrogen and R$^3$ is n-C$_{11}$ alkyl.

2. A chemical compound according to claim 1 wherein L is —COOR$^4$, cyano or a group —C(=G)—D—R$^6$; R$^2$ is hydrogen, C$_1$–C$_7$alkyl, C$_3$–C$_7$alkenyl, C$_3$–C$_7$alkynyl, C$_5$–C$_7$cycloalkenyl, C$_3$–C$_7$cycloalkyl or mono-, di- or trihaloC$_1$–C$_5$alkyl; said C$_1$–C$_7$alkyl, C$_5$–C$_7$cycloalkenyl or C$_3$–C$_7$cycloalkyl being optionally substituted with C$_1$–C$_5$alkyl; and R$^3$ is C$_4$–C$_{13}$alkyl, C$_5$–C$_7$cycloalkenyl or C$_3$–C$_7$cycloalkyl each optionally substituted with C$_1$–C$_5$alkyl.

3. A chemical compound according to claim 2 wherein D is —N(R$^7$)— or —N(R$^8$)—O—; and R$^4$, R$^6$, R$^7$ and R$^8$ are hydrogen or C$_1$–C$_5$alkyl.

4. A chemical compound according to claim 1 wherein the compound is methyl 1-(dicyclohexylmethyl)-1H-imidazole-5-carboxylate.

5. A herbicidal composition comprising an inert carrier and, if desired, other adjuvants, and as active ingredient a herbicidally-effective amount of a compound having the formula:

or a stereoisomeric form thereof, or a salt thereof, wherein

R$^1$ is hydrogen or mercapto;
R$^2$ is hydrogen, C$_1$–C$_7$alkyl, C$_3$–C$_7$alkenyl, C$_3$–C$_7$alkynyl, C$_3$–C$_7$cycloalkyl, C$_5$–C$_7$cycloalkenyl; said C$_1$–C$_7$alkyl, C$_3$–C$_7$alkenyl, C$_3$–C$_7$alkynyl, C$_3$–C$_7$cycloalkyl, C$_5$–C$_7$cycloalkenyl being optionally substituted with one to three radicals selected from C$_1$–C$_5$alkyl, C$_1$–C$_5$alkyloxy, hydroxyC$_1$–C$_5$alkyl, C$_1$–C$_5$alkyloxyC$_1$–C$_5$alkyl and halo;
R$^3$ is C$_4$–C$_{13}$alkyl, C$_3$–C$_7$cycloalkyl, or C$_5$–C$_7$cycloalkenyl each unsubstituted or substituted with one to three radicals selected from C$_1$–C$_5$alkyl, C$_1$–C$_5$alkyloxy, hydroxyC$_1$–C$_5$alkyl, C$_1$–C$_5$alkyloxyC$_1$–C$_5$alkyl and halo;
L is cyano, —COOR$^4$,

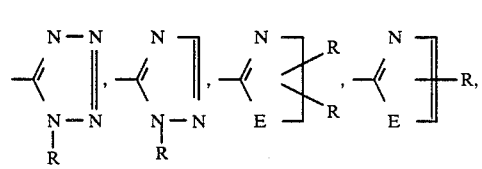

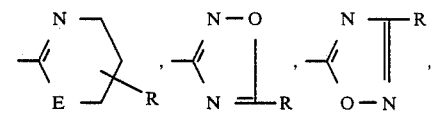

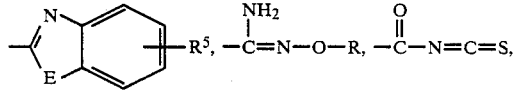

or a group of —C(=G)—D—R$^6$;

R$^4$ is hydrogen, C$_1$–C$_7$alkyl, mono-, di- or trihaloC$_1$–C$_5$alkyl, C$_3$–C$_7$alkenyl, C$_3$–C$_7$alkynyl, C$_3$–C$_7$cycloalkyl, C$_1$–C$_7$alkyloxyC$_1$–C$_7$alkyl or arylC$_1$–C$_5$alkyl;

E is oxygen, sulfur or —NR—;
R is hydrogen or C$_1$–C$_5$alkyl;
G is =N—R, oxygen or sulfur;
D is sulfur, —N(R$^7$)—, —N(R$^8$)—NH—, —N(R$^8$)—O—,

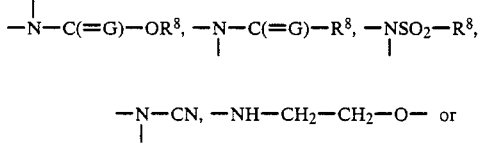

R⁶, R⁷ and R⁸ are independently selected from hydrogen, $C_1$-$C_5$alkyl, $C_3$-$C_5$alkenyl, $C_3$-$C_5$alkynyl, $C_3$-$C_7$cycloalkyl or $C_1$-$C_5$alkyl substituted with aryl, $C_3$-$C_7$cycloalkyl, $C_3$-$C_7$cycloalkyloxy, $C_1$-$C_5$alkyloxy, hydroxy, carboxyl or $C_1$-$C_5$alkyloxycarbonyl; whereas R⁸ may also be aryl; or R⁶ and R⁷ together with the nitrogen atom to which they are attached may form a piperidinyl, pyrrolidinyl, 2-oxopiperidinyl, 2-oxopyrrolidinyl, morpholinyl, thiomorpholinyl, piperazinyl or 4-($C_1$-$C_5$alkyl)piperazinyl ring, each unsubstituted or substituted with one to three $C_1$-$C_5$alkyl groups;

R⁵ is hydrogen, $C_1$-$C_5$alkyl, $C_1$-$C_5$alkyloxy, halo, trifluoromethyl, difluoromethoxy, cyano, nitro, amino, mono- and di$C_1$-$C_5$alkylamino or $C_1$-$C_5$alkylcarbonylamino; and aryl is phenyl optionally substituted with one to three substituents each independently selected from $C_1$-$C_5$alkyl, $C_1$-$C_5$alkyloxy and halo.

6. A herbicidal composition according to claim 5 wherein L is —COOR⁴, cyano or a group —C(=G)—D—R⁶; R² is hydrogen, $C_1$-$C_7$alkyl, $C_3$-$C_7$alkenyl, $C_3$-$C_7$alkynyl, $C_5$-$C_7$cycloalkenyl, $C_3$-$C_7$cycloalkyl or mono-, di- or trihalo$C_1$-$C_5$alkyl; said $C_1$-$C_7$alkyl, $C_5$-$C_7$cycloalkenyl or $C_3$-$C_7$cycloalkyl being optionally substituted with $C_1$-$C_5$alkyl; and R³ is $C_4$-$C_{13}$alkyl, $C_5$-$C_7$cycloalkenyl or $C_3$-$C_7$cycloalkyl each optionally substituted with $C_1$-$C_5$alkyl.

7. A herbicidal composition according to claim 6 wherein D is —N(R⁷)— or —N(R⁸)—O—; and R⁴, R⁶, R⁷ and R⁸ are hydrogen or $C_1$-$C_5$alkyl.

8. A herbicidal composition according to claim 7 wherein the compound is methyl 1-(dicyclohexylmethyl)-1H-imidazole-5-carboxylate.

9. A method for controlling weeds, which method comprises applying to said weeds or to the locus thereof a herbicidally effective amount of a chemical compound having the formula:

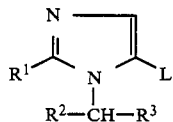   (I)

or a stereoisomeric form thereof, or a salt thereof, wherein

R¹ is hydrogen or mercapto;

R² is hydrogen, $C_1$-$C_7$alkyl, $C_3$-$C_7$alkenyl, $C_3$-$C_7$alkynyl, $C_3$-$C_7$cycloalkyl, $C_5$-$C_7$cycloalkenyl; said $C_1$-$C_7$alkyl, $C_3$-$C_7$alkenyl, $C_3$-$C_7$alkynyl, $C_3$-$C_7$cycloalkyl, $C_5$-$C_7$cycloalkenyl being optionally substituted with one to three radicals selected from $C_1$-$C_5$alkyl, $C_1$-$C_5$alkyloxy, hydroxy$C_1$-$C_5$alkyl, $C_1$-$C_5$alkyloxy$C_1$-$C_5$alkyl and halo;

R³ is $C_4$-$C_{13}$alkyl, $C_3$-$C_7$cycloalkyl, or $C_5$-$C_7$cycloalkenyl each unsubstituted or substituted with one to three radicals selected from $C_1$-$C_5$alkyl, $C_1$-$C_5$alkyloxy, hydroxy$C_1$-$C_5$alkyl, $C_1$-$C_5$alkyloxy$C_1$-$C_5$alkyl and halo;

L is cyano, —COOR⁴,

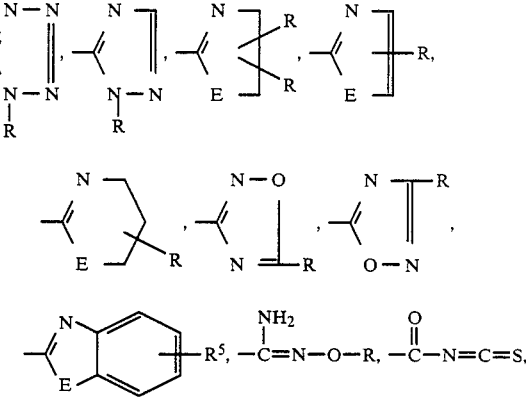

or a group of —C(=G)—D—R⁶;

R⁴ is hydrogen, $C_1$-$C_7$alkyl, mono-, di- or trihalo$C_1$-$C_5$alkyl, $C_3$-$C_7$alkenyl, $C_3$-$C_7$alkynyl, $C_3$-$C_7$cycloalkyl, $C_1$-$C_7$alkyloxy$C_1$-$C_7$alkyl or aryl$C_1$-$C_5$alkyl;

E is oxygen, sulfur or —NR—;

R is hydrogen or $C_1$-$C_5$alkyl;

G is =N—R, oxygen or sulfur;

D is sulfur, —N(R⁷)—, —N(R⁸)—NH—, —N(R⁸)—O—,

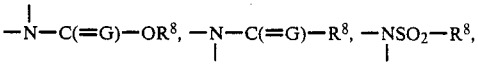

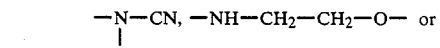

R⁶, R⁷ and R⁸ are independently selected from hydrogen, $C_1$-$C_5$alkyl, $C_3$-$C_5$alkenyl, $C_3$-$C_5$alkynyl, $C_3$-$C_7$cycloalkyl or $C_1$-$C_5$alkyl substituted with aryl, $C_3$-$C_7$cycloalkyl, $C_3$-$C_7$cycloalkyloxy, $C_1$-$C_5$alkyloxy, hydroxy, carboxyl or $C_1$-$C_5$alkyloxycarbonyl; whereas R⁸ may also be aryl; or R⁶ and R⁷ together with the nitrogen atom to which they are attached may form a piperidinyl, pyrrolidinyl, 2-oxopiperidinyl, 2-oxopyrrolidinyl, morpholinyl, thiomorpholinyl, piperazinyl or 4-($C_1$-$C_5$alkyl)piperazinyl ring, each unsubstituted or substituted with one to three $C_1$-$C_5$alkyl groups;

R⁵ is hydrogen, $C_1$-$C_5$alkyl, $C_1$-$C_5$alkyloxy, halo, trifluoromethyl, difluoromethoxy, cyano, nitro, amino, mono- and di$C_1$-$C_5$alkylamino or $C_1$-$C_5$alkylcarbonylamino; and aryl is phenyl optionally substituted with one to three substituents each independently selected from $C_1$-$C_5$alkyl, $C_1$-$C_5$alkyloxy and halo.

10. A method according to claim 9 for selectively controlling weeds in crops of useful plants.

11. A method according to claim 10 wherein the crop is rice, maize or cereals.

12. A method according to claim 10 wherein the crop is rice and the rice is transplanted rice.

13. A method according to claim 11, wherein 0.01 to 5 kg of active ingredient per hectate are applied to areas where rice crops are grown.

14. A method according to claim 13 wherein 0.05 to 1 kg of the active ingredient is applied per hectare after transplanting the rice plantlets.

15. A method according to claim 9 wherein L is $-COOR^4$, cyano or a group $-C(=G)-D-R^6$; $R^2$ is hydrogen, $C_1-C_7$alkyl, $C_3-C_7$alkenyl, $C_3-C_7$alkynyl, $C_5-C_7$cycloalkenyl, $C_3-C_7$cycloalkyl or mono-, di- or trihalo$C_{1-5}$alkyl; said $C_1-C_7$alkyl, $C_5-C_7$cycloalkenyl or $C_3-C_7$cycloalkyl being optionally substituted with $C_1-C_5$alkyl; and $R^3$ is $C_4-C_{13}$alkyl, $C_5-C_7$cycloalkenyl or $C_3-C_7$cycloalkyl each optionally substituted with $C_1-C_5$alkyl.

16. A method according to claim 15 wherein D is $-N(R^7)-$ or $-N(R^8)-O$; and $R^4$, $R^6$, $R^7$ and $R^8$ are hydrogen or $C_1-C_5$alkyl.

17. A method according to claim 16 wherein the compound is methyl 1-(dicyclohexylmethyl)-1H-imidazole-5-carboxylate.

* * * * *